(12) United States Patent
Hidaka et al.

(10) Patent No.: US 11,150,182 B2
(45) Date of Patent: Oct. 19, 2021

(54) TESTING METHOD AND TESTING SYSTEM (71) Applicant: YOKOGAWA ELECTRIC CORPORATION, Tokyo (JP)

(72) Inventors: Yoshihisa Hidaka, Musashino (JP); Gen Matsuno, Musashino (JP); Shigeru Takezawa, Musashino (JP); Hideko Tanaka, Musashino (JP); Kaori Sakuma, Musashino (JP); Akihiro Murata, Musashino (JP); Toshiki Ohara, Musashino (JP)

(73) Assignee: YOKOGAWA ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 16/648,058

(22) PCT Filed: Sep. 5, 2018

(86) PCT No.: PCT/JP2018/032905
§ 371 (c)(1),
(2) Date: Mar. 17, 2020

(87) PCT Pub. No.: WO2019/058971
PCT Pub. Date: Mar. 28, 2019

(65) Prior Publication Data
US 2020/0256792 A1    Aug. 13, 2020

(30) Foreign Application Priority Data
Sep. 19, 2017    (JP) .............................. JP2017-179324

(51) Int. Cl.
*G01N 21/359*    (2014.01)
*G01N 1/24*    (2006.01)
(Continued)

(52) U.S. Cl.
CPC ............ *G01N 21/359* (2013.01); *G01N 1/24* (2013.01); *G01N 21/3504* (2013.01);
(Continued)

(58) Field of Classification Search
CPC .. G01N 21/359; G01N 21/3504; G01N 21/35; G01N 21/8507; G01N 2021/8578
See application file for complete search history.

(56) References Cited

U.S. PATENT DOCUMENTS 4,560,873 A    12/1985    McGowan et al.
4,958,076 A *    9/1990    Bonne ................ G01N 21/3504
250/343

(Continued)

FOREIGN PATENT DOCUMENTS

DE    102011076222 A1    11/2012
DE    202016102007 U1    7/2017
JP    2001-009268 A    1/2001

OTHER PUBLICATIONS

Blair D. Macdonald, "Response to Judge Alsup's Question No. 2: What's the molecular reason that CO2 is a greenhouse gas, unlike oxygen and nitrogen", Jun. 26, 2018 (Year: 2018).*

*Primary Examiner* — Maurice C Smith
(74) *Attorney, Agent, or Firm* — Osha Bergman Watanabe & Burton LLP (57)    ABSTRACT

A method for testing an analysis apparatus that analyzes a first fluid flowing through a pipe using light that has passed through a probe attached to and disposed inside the pipe such that a portion of a light path passes outside a housing of the probe. The method includes: after a second fluid that absorbs less of the light than the first fluid has been introduced into the pipe, introducing a third fluid having predetermined absorption characteristics into the housing of the
(Continued)

probe; and analyzing the absorption characteristics of the third fluid using the light that has passed through the probe.

10 Claims, 6 Drawing Sheets

(51) Int. Cl.
*G01N 21/3504* (2014.01)
*G01N 21/3577* (2014.01)
*G01N 21/85* (2006.01)

(52) U.S. Cl.
CPC ......... *G01N 21/3577* (2013.01); *G01N 21/85* (2013.01); *G01N 2021/8578* (2013.01)

(56) References Cited

U.S. PATENT DOCUMENTS

| | | | |
|---|---|---|---|
| 2012/0260715 A1* | 10/2012 | Miyai | G01N 21/274 |
| | | | 73/1.07 |
| 2013/0161544 A1* | 6/2013 | Ohnishi | G01N 21/8507 |
| | | | 250/564 |
| 2014/0002823 A1* | 1/2014 | Nakatani | G01N 21/05 |
| | | | 356/439 |
| 2014/0183380 A1* | 7/2014 | Ukon | G01N 21/3504 |
| | | | 250/573 |
| 2015/0377776 A1 | 12/2015 | Xie | |
| 2016/0231233 A1* | 8/2016 | Wang | G02B 6/1226 |
| 2017/0082537 A1* | 3/2017 | Ido | G01N 21/8507 |
| 2017/0131199 A1* | 5/2017 | Skouboe | G01N 21/8507 |
| 2018/0252639 A1* | 9/2018 | Spartz | G01N 21/94 |

* cited by examiner

TESTING METHOD AND TESTING SYSTEM

CROSS-REFERENCE TO RELATED APPLICATION

The present application claims priority to and the benefit of Japanese Patent Application No. 2017-179324 filed Sep. 19, 2017, the entire contents of which are incorporated herein by reference.

BACKGROUND

Technical Field

The present invention relates to calibration of a testing method and a testing system, such as a component analysis system for liquified natural gas (LNG) using a Fourier transform-near infrared spectrometer (FT-NIR). The present invention can be applied to online measurement in LNG production, LNG terminals, and various plants that handle LNG as a raw material.

Description of Related Art

An FT-NIR is an analysis apparatus for detecting the absorption spectrum from light obtained when near-infrared light is irradiated onto and passes through an object of analysis. Normally, a performance test is performed on the hardware of the FT-NIR at the time of shipment. After delivery, a test is run to confirm that predetermined aspects of performance have not changed over time.

The hardware performance is tested by the following procedures.

Case 1: another measurement device, capable of measuring the same object of analysis as the FT-NIR to be tested, is prepared. The measurement results of the other measurement device and the measurement results of the FT-NIR are compared to check for any difference. When there is a difference, the FT-NIR is calibrated so that the measurement results of the FT-NIR and the measurement results of the other measurement device match. A gas chromatograph, for example, is used as the other measurement device.

Case 2: a sample with a known laboratory value indicating the composition is placed in a measurement cell as an object of measurement, and the measurement results of the FT-NIR and the laboratory value are compared to check for any difference. When there is a difference, the FT-NIR is calibrated so that the measurement results of the FT-NIR and the laboratory value match.

PATENT LITERATURE

PTL 1: JP2001-9268A

In the aforementioned case 1, another measurement device is necessary, and the FT-NIR cannot be tested alone. In case 2, a sample with a known laboratory value needs to be prepared in advance. If the object of measurement is a substance that has a lower boiling point than room temperature, such as LNG, or a highly volatile substance, the composition changes due to vaporization. It is therefore difficult to prepare a standard sample. When a standard sample is the object of measurement, it is necessary to have the standard sample flow through a process pipe in a plant or to detach a measurement probe from a pipe to fill the measurement probe with the standard sample. This procedure affects plant operations.

SUMMARY

The present invention provide a testing method and testing system that can increase testing efficiency.

A method, according to one or more embodiments, is for testing an analysis apparatus that performs analysis using light that has passed through a probe attached to a pipe through which a first fluid that is an object of analysis flows, the probe being attached in such a manner that a portion of a light path passes outside a housing of the probe and is disposed inside the pipe, the method including a first process of introducing a third fluid inside the housing of the probe in a state such that a second fluid that absorbs less of the light than the first fluid has been introduced into the pipe, the third fluid having known (or predetermined) absorption characteristics, and a second process of analyzing absorption characteristics of the third fluid using the light that has passed through the probe.

The method, according to one or more embodiments, for testing an analysis apparatus may further include a third process, after completion of the second process, of replacing the third fluid introduced inside the housing with the second fluid.

In one or more embodiments, the housing may include a recess that is recessed inward, and the portion of the light path may pass through the recess.

In one or more embodiments, the light may be near-infrared light, and the second fluid may be nitrogen.

In one or more embodiments, the first fluid flowing through the pipe may be in the liquid phase, and the second fluid and the third fluid introduced into the housing may be in the gas phase.

A system, according to one or more embodiments, is for testing an analysis apparatus that performs analysis using light that has passed through a probe attached to a pipe through which a first fluid that is an object of analysis flows, the probe being attached in such a manner that a portion of a light path passes outside a housing of the probe and is disposed inside the pipe, the system including a first container containing a second fluid that absorbs less of the light than the first fluid, a second container containing a third fluid that has known (or predetermined) absorption characteristics, and an introducer (or conduit) configured to introduce the second fluid contained in the first container or the third fluid contained in the second container inside the housing of the probe.

The system, according to one or more embodiments, for testing an analysis apparatus may further include a pump configured to suction a fluid introduced inside the housing of the probe.

The testing method and testing system according to one or more embodiments of the present invention can improve testing efficiency. For example, it is not necessary during testing to detach the probe from the pipe, to use another measurement device, to have a standard fluid flow through the pipe, or to separately prepare a standard sample.

DETAILED DESCRIPTION

Embodiments of a testing method and a testing system are now described with reference to the drawings. To facilitate comprehension, the case of a testing system of one or more embodiments being applied to an LNG analysis system, and of an analysis apparatus being applied to an FT-NIR, is mainly described below as an example.

Figure 1:
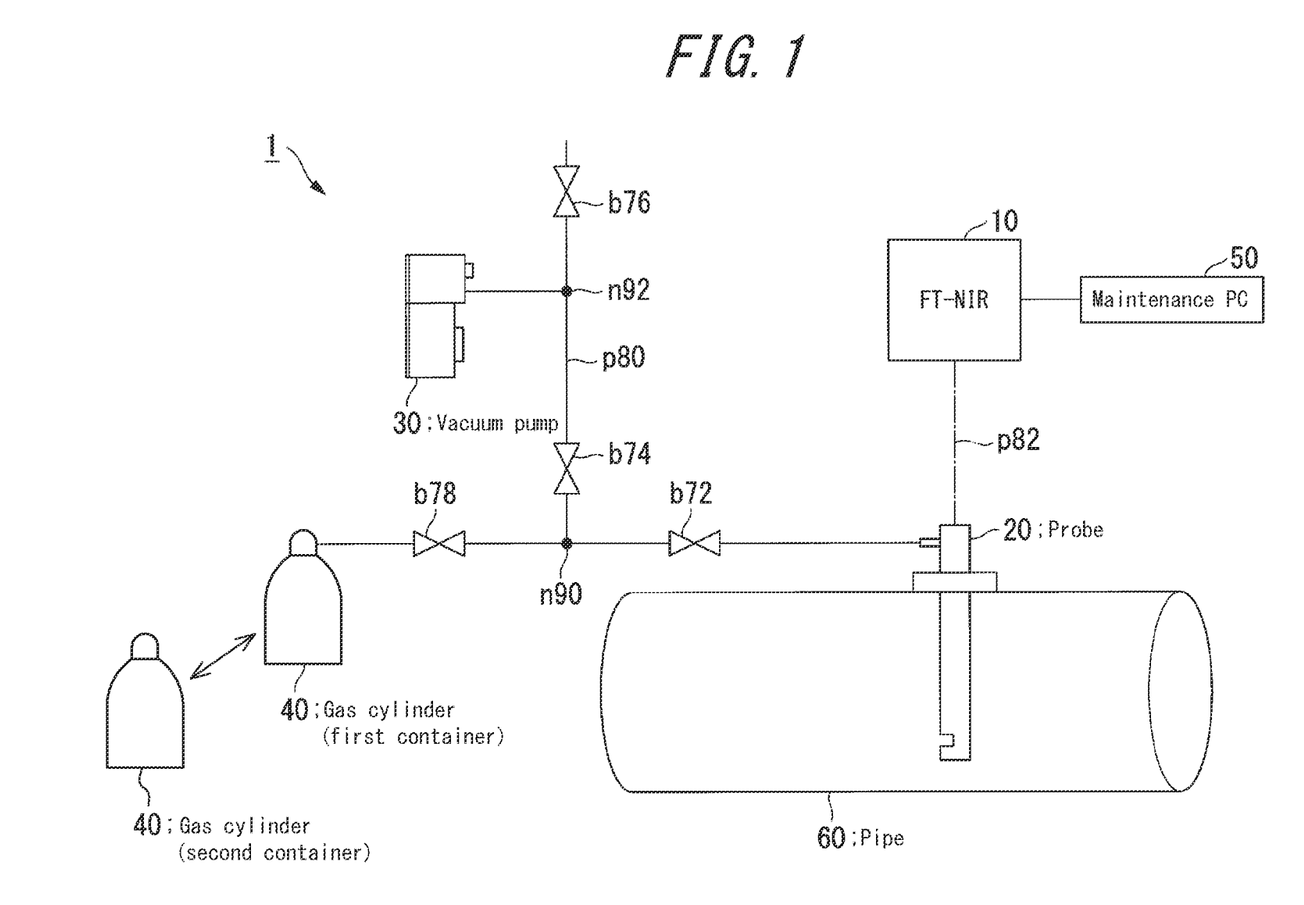
FIG. 1 illustrates the schematic configuration of a testing system according to one or more embodiments.

FIG. 1 illustrates the schematic configuration of a testing system 1 according to one or more embodiments.

The testing system 1 includes an FT-NIR 10, a probe 20, a vacuum pump 30, a gas cylinder 40, and a maintenance PC 50.

The FT-NIR 10 connects to the probe 20 via an optical fiber p82. The light emitted from a light source of the FT-NIR 10 enters the probe 20 through the optical fiber p82. The light emitted from the probe 20 enters the FT-NIR 10 through the optical fiber p82.

The FT-NIR 10 is an analysis apparatus including the light source that emits light, a detector that detects incident light, and an analyzer that analyzes the spectrum of detected light. The light source is, for example, a halogen lamp that emits near-infrared light. The light emitted by the light source is used as detection light for detecting the absorption characteristics of an object of analysis. The detection light is also referred to as probe light. Near-infrared light is an electromagnetic wave with a wavelength of 0.7 µm to 2.5 µm. This wavelength range becomes the wavelength range over which analysis is possible.

The components of LNG, which is a first fluid that becomes an object of analysis, has distinguishing absorption characteristics within this wavelength range. The analyzer derives an absorption spectrum by calculating absorption as the ratio of the emission intensity from the light source to the detection intensity of detected light of each wavelength. The analyzer includes a Fourier transform spectrometer. Based on the derived absorption spectrum, the analyzer calculates the concentration of the object of testing and the composition of each component. To calculate the concentration and the composition of each component, the pattern of the absorption spectrum of each component, for example, is set in the analyzer in advance. The analyzer uses the set patterns to perform multivariate analysis on the derived absorption spectrum.

The probe 20 includes a light path over which light entering through the optical fiber p82 propagates. The light passes through the object of analysis in a portion of the light path. The light that has passed through the object of analysis is emitted into the optical fiber p82. In one or more embodiments, a first fluid that becomes the object of analysis flows inside a pipe 60. The probe 20 is therefore attached to the pipe 60 in such a manner that a portion of the light path is disposed inside the pipe 60 through which the first fluid flows. The housing of the probe 20 has a shape that allows a portion of the light path to pass outside the housing and the other portion to pass through the inside of the housing. A recess that is recessed inward is provided in a portion of the housing, and the light path is provided so as to traverse the recess. The inside of the housing of the probe 20 is also referred to below simply as "inside the probe 20".

The vacuum pump 30 suctions fluid located inside a conduit p80 to vacuum the conduit p80 and the inside of the probe 20 connected to the conduit p80 as another container.

The gas cylinder 40 is a container that contains gas, which has predetermined components, at a higher pressure than atmospheric pressure. In the example described below, one of a gas cylinder 40 filled with nitrogen ($N_2$) gas as the second fluid and a gas cylinder 40 filled with a standard gas as the third fluid is selectively used in accordance with the procedures. The gas cylinder 40 filled with nitrogen gas is also referred to below as a "nitrogen gas cylinder", and the gas cylinder 40 filled with the standard gas is also referred to as a "standard gas cylinder". The standard gas may be a gas that has distinguishing absorption characteristics in the wavelength range subjected to analysis and that has known components. For example, methane ($CH_4$) can be used as the standard gas.

The maintenance PC 50 is a personal computer (PC) that functions as a control apparatus for executing a sequence of procedures of the analysis method according to one or more embodiments. The maintenance PC 50 has a computer system that includes an arithmetic device such as a central processing unit (CPU). The arithmetic device has the function of a control apparatus for executing processes as instructed by commands described in installed application software.

From the FT-NIR 10, the maintenance PC 50 can acquire the analysis results, i.e. the absorption spectrum along with the concentration and composition of the object of testing, and the test results, i.e. the test values or the success/failure of the test. The maintenance PC 50 tests whether the absorption spectrum acquired for the standard gas satisfies a predetermined standard. This test is referred to below as a calibration test. Calibration is typically divided into hardware calibration and modeling curve/calibration curve calibration. The calibration in one or more embodiments relates to hardware calibration.

The procedures for the calibration test as described below do not include operations or processing to adjust the hardware of the FT-NIR 10 or the like.

The probe 20, the vacuum pump 30, and the gas cylinder 40 are connected via the conduit p80 that allows a fluid to pass therebetween. Two branches (nodes) n90, n92 and four valves b72, b74, b76, b78 are provided in the conduit p80. The valve b72 is disposed between the branch n90 and the probe 20. The probe 20 is connected to the conduit p80 via a stop valve 240 (described below). The valve b74 is disposed between the two branches n90, n92. The valve b76 is disposed between the branch n92 and one end of the conduit p80. The valve b78 is disposed between the gas cylinder 40 and the branch n90. The valves b72, b74, b76, b78 and the stop valve 240 can each adjust the degree of opening of the inside of the conduit p80. The inside of the probe 20 can be vacuumized by the opening and closing of the valves b72, b74, b76, b78. Gas accumulated in the gas cylinder 40 can be introduced into the probe 20 by the opening and closing of the valves b72, b74, b76, b78. The valves b72, b78 and the conduit p80 function as an introducer for introducing the gas accumulated in the gas cylinder 40 into the probe 20.

Setting the valve b72 and the like to open up the inside of the conduit p80 for fluid to flow is referred to as "opening the valve b72 and the like". Setting the valve b72 and the like to close off the inside of the conduit p80 so that fluid does not flow is referred to as "closing the valve b72 and the like". The control to open and close the valves b72, b74, b76, b78 may be executed by the maintenance PC 50 or by another control apparatus.

In one or more embodiments, a third fluid with known (or predetermined) absorption characteristics can be introduced from the gas cylinder 40, in which the third fluid is accumulated, into the probe 20 in a state such that a second fluid that absorbs less of the detection light than the first fluid has been introduced into the pipe 60, as described below. Subsequently, the FT-NIR 10 can analyze the absorption characteristics of the third fluid using the light entering from the probe 20.

After the absorption characteristics of the third fluid are analyzed, the vacuum pump 30 vacuumizes the inside of the housing of the probe 20. The gas cylinder 40 in which the third fluid is accumulated is exchanged with the gas cylinder 40 in which the second fluid is accumulated, and the second fluid is introduced inside the housing of the probe 20 from the exchanged gas cylinder 40. Consequently, the third fluid introduced inside the housing of the probe 20 is replaced by the second fluid. The second fluid is nitrogen, and the third fluid is a standard gas. The standard gas is a gas with known absorption characteristics of light.

Figure 2:
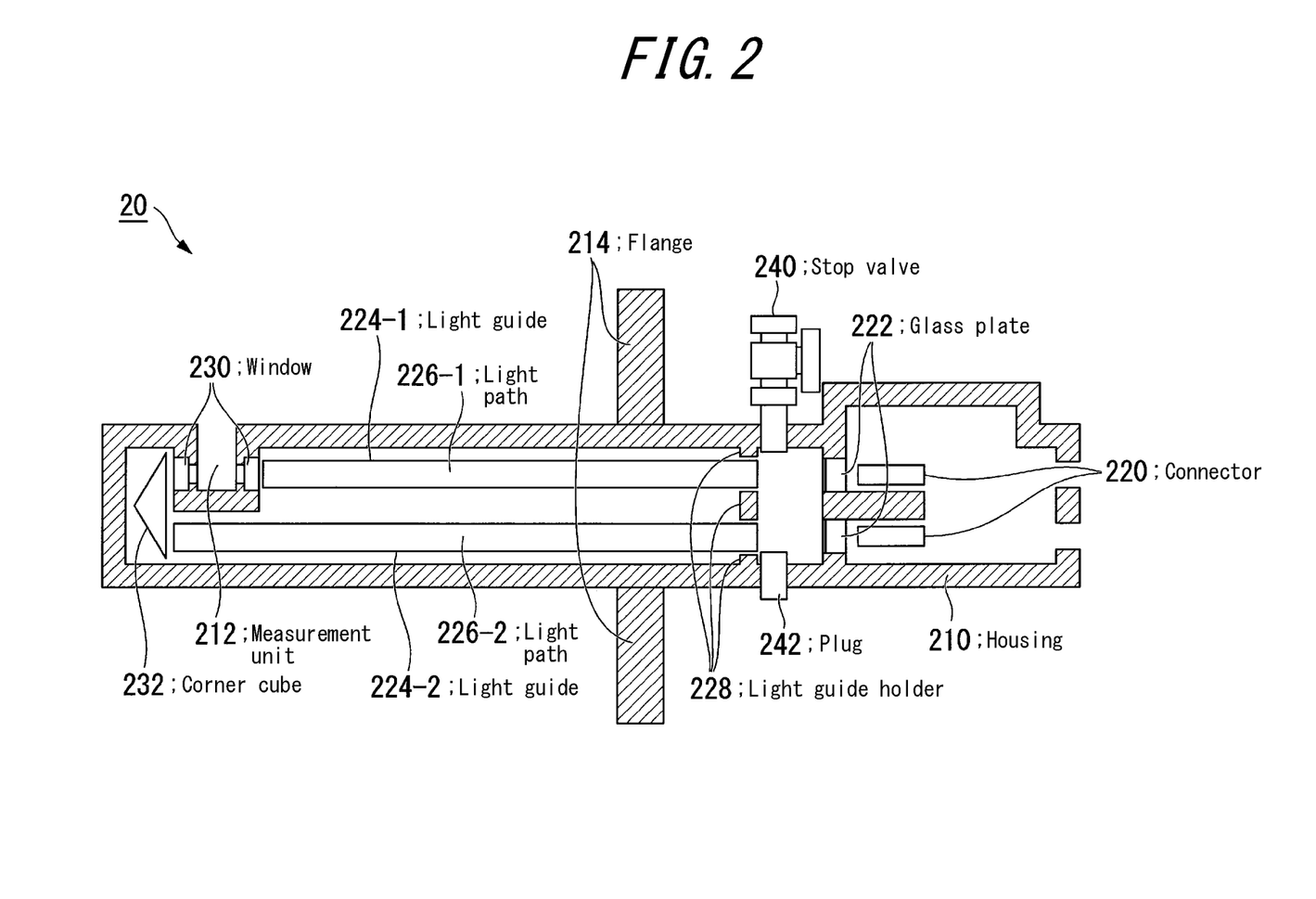
FIG. 2 is a cross-sectional view of an example configuration of a probe according to one or more embodiments.

Next, an example configuration of the probe 20 according to one or more embodiments is described.

FIG. 2 is a cross-sectional view of an example configuration of the probe 20 according to one or more embodiments.

The probe 20 includes a housing 210, a flange 214, a connector 220, a glass plate 222, two light guides 224, a light guide holder 228, windows 230, a corner cube 232, the stop valve 240, and a plug 242.

The housing 210 has an elongated shape overall and includes a space therein that can be filled with fluid. A measurement unit 212, which is a recess that is recessed (or depressed) inward from the surrounding area, is positioned closer to one end of the housing 210 in the longitudinal direction than the other end. The flange 214, which surrounds the outer periphery of the housing 210, is disposed at a position closer to the other end of the housing 210 in the longitudinal direction than the central portion. The one end of the housing 210 in the longitudinal direction is also referred to below as "one end of the probe 20", and the other end of the housing 210 in the longitudinal direction is also referred to below as the "other end of the probe 20".

In the example in FIG. 2, the left end of the housing 210 is the "one end of the probe 20", and the right end is the "other end of the probe 20".

The flange 214 is a disk-shaped member that has a flat surface perpendicular to the longitudinal direction of the housing 210 when the flange 214 is disposed on the housing 210. This flat surface is pressed against the outer surface of the pipe 60 to fix the probe 20. The flange 214 thereby suppresses leakage of fluid from the opening of the pipe 60 through which the probe 20 is inserted.

Two openings are provided on the side surface of the housing 210 at positions closer to the other end of the probe 20 than the flange 214. The stop valve 240 and the plug 242 are disposed at the two openings. The stop valve 240 is a valve that connects to the conduit p80 and can adjust the degree of opening of the inside of the housing 210 with respect to the inside of the conduit p80. At the time of regular measurement, the stop valve 240 seals the inside of the housing 210 with respect to the inside of the conduit p80. When a fluid is introduced inside the housing 210 from the gas cylinder 40 via the conduit p80, or when the inside of the housing 210 is vacuumized, the stop valve opens the inside of the housing 210 with respect to the inside of the conduit p80.

Setting the stop valve 240 to seal the inside of the housing 210 with respect to the inside of the conduit p80 is referred to below as "closing the stop valve 240" and setting the stop valve 240 to open the inside of the housing 210 with respect to the inside of the conduit p80 is referred to below as "opening the stop valve 240".

The plug 242 is a member that seals the opening into which the plug 242 is inserted. The plug 242 seals the opening so that the fluid filling the inside of the housing 210 does not leak outside.

Two openings are provided at the other end of the probe 20. One optical fiber p82 is inserted through each of the openings.

The glass plate 222 is provided in parallel to a surface perpendicular to the longitudinal direction of the probe 20 at a position closer to the other end of the probe 20 than the stop valve 240 or the plug 242. The connector 220 is disposed facing the side of the glass plate 222 closer to the other end of the probe 20. The connector 220 allows attachment of the two inserted optical fibers p82.

Light guides 224-1, 224-2 are disposed inside the housing 210 in parallel with the longitudinal direction of the housing 210. The light guides 224-1, 224-2 are each a tubular member having a smooth inner surface and are coated with a substance that reflects light. The light guides 224-1, 224-2 are, for example, made of stainless steel. Light paths 226-1, 226-2 are therefore formed inside the light guides 224-1, 224-2.

In the example in FIG. 2, the left end of the housing 210 is the "one end of the light guides 224-1, 224-2", and the right end is the "other end of the light guides 224-1, 224-2".

The light guide holder 228 is disposed inside the housing 210 at a position closer to the flange 214 than the stop valve 240 or the plug 242.

The light guide holder 228 is a member that fixes the outer surface of the light guides 224-1, 224-2, near the other end thereof, to the housing 210.

The windows 230 are provided on two intersecting surfaces that form the measurement unit 212 and intersect side surfaces intersecting the longitudinal direction of the housing 210. The two intersecting surfaces include an intersecting surface closer to the other end of the probe 20 and an intersecting surface closer to the one end of the probe 20. The intersecting surface closer to the other end of the probe 20 faces the one end of the light guide 224-1.

The corner cube 232 is disposed at a position closer to the one end of the probe 20 than the measurement unit 212 in the housing 210.

The corner cube 232 is an optical component shaped as the vertex of a cube formed by assembling three flat reflectors at right angles to each other. In the example in FIG. 2, however, only two of the three reflectors are depicted, and the remaining reflector is not illustrated.

With this configuration, light that is emitted from the one end of the light guide 224-1 passes through the measurement unit 212 via the windows 230 and is incident on the corner cube 232. The light incident on the corner cube 232 is reflected by the reflectors and is incident on the one end of the light guide 224-2.

The glass plate 222 and the windows 230 are formed by a substance that transmits light without absorbing or reflecting the light (such as sapphire glass). The glass plate 222 and the windows 230 form seals so that the fluid filling the inside of the housing 210 does not leak outside.

Accordingly, the light incident from one of the optical fibers p82 connected to the connector 220 passes through the light path that includes the glass plate 222, the light path 226-1, the windows 230, the corner cube 232, the light path 226-2, and the glass plate 222 and is emitted onto the other optical fiber p82. The measurement unit 212 thus forms a portion of the light path from the entrance face of one of the optical fibers p82 to the exit face of the other optical fiber. The diameter of a cross-section perpendicular to the longitudinal direction of the housing 210 is nearly constant throughout the portion of the housing 210 where the measurement unit 212 is not formed. In the section from the glass plate 222 to the corner cube 232, a section of the light path 226-1 that is inside the housing 210 and a section that is outside the housing 210 are therefore positioned along the same straight line. This makes it relatively easy to adjust the position and orientation of members such as the light guide 224-1 and the corner cube 232 that form the light path.

In a regular measurement state, nitrogen fills the inside of the housing 210 as a purge gas, and the probe 20 is disposed inside the pipe 60. LNG flowing inside the pipe 60 passes through the measurement unit 212, which is outside the housing 210, as the object of measurement. Among the light that passes through the measurement unit 212, a component of a predetermined wavelength is therefore absorbed by the object of measurement. This wavelength component that is absorbed differs depending on the chemical structure of the molecule. Hence, the shape of the optical spectrum differs. Absorption increases as the concentration of the object of measurement is higher. The FT-NIR 10 can use the acquired optical spectrum to calculate the concentration and composition of the object of measurement.

Figure 3:
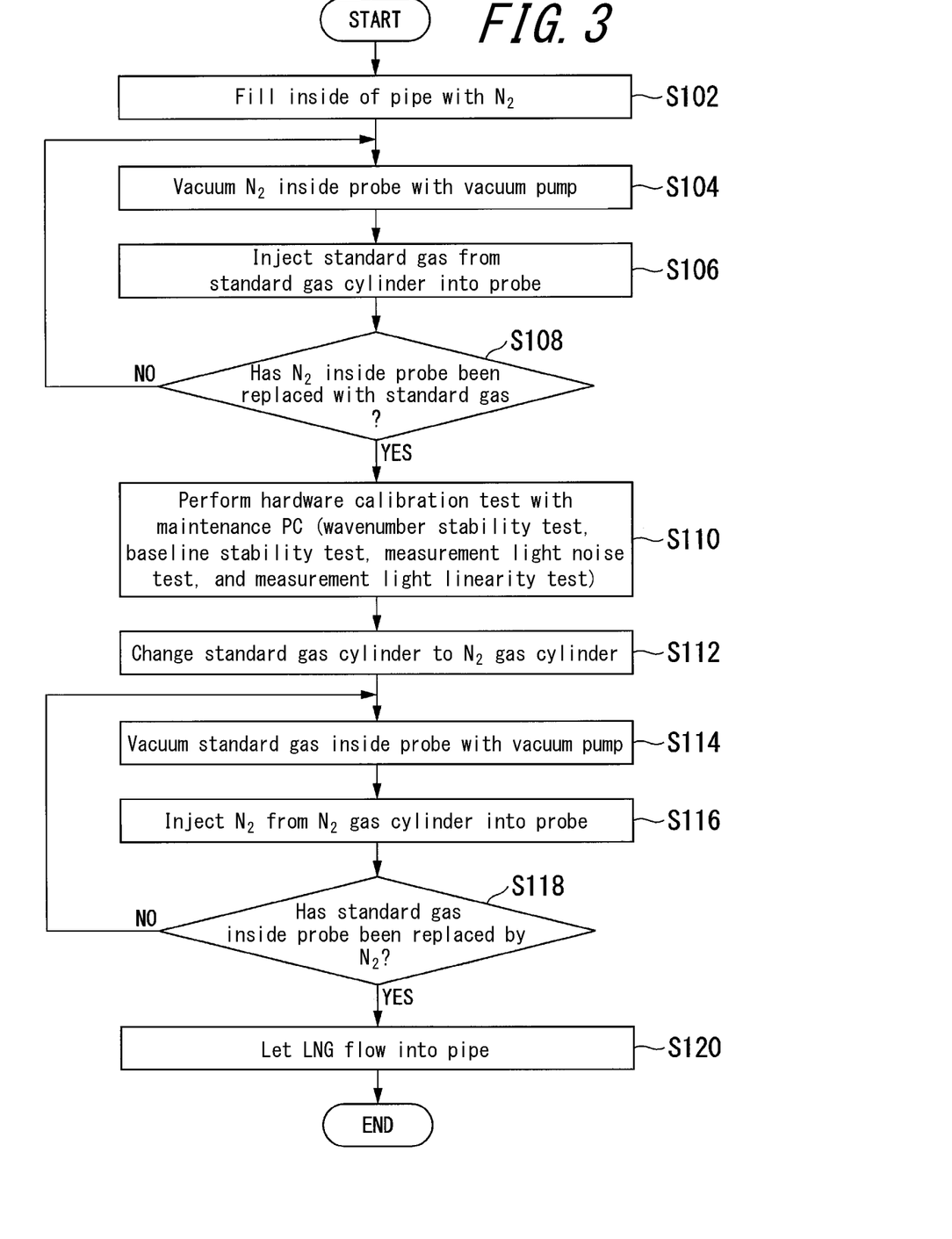
FIG. 3 is a flowchart illustrating an example of a testing method according to one or more embodiments.

An example of a testing method according to one or more embodiments is described next.

FIG. 3 is a flowchart illustrating an example of a testing method according to one or more embodiments.

Figure 4:
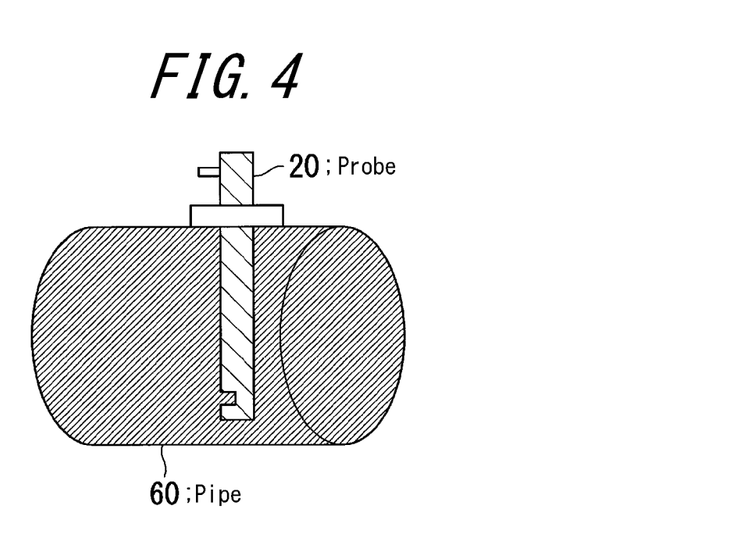
FIG. 4 illustrates the types of fluids in a probe and a pipe before testing according to one or more embodiments.

The testing method in FIG. 3 illustrates an example of starting when the state of the probe 20 is in a normal usage state. The testing method illustrated in FIG. 3 is typically performed while operations are suspended, such as during routine inspection of the pipe 60. In the regular usage state, the inside of the housing 210 of the probe 20 is filled with nitrogen, and LGN flows inside the pipe 60 (see FIG. 4). In FIG. 4, the diagonal lines from upper right to lower left indicate LNG, and the diagonal lines from upper left to lower right indicate nitrogen. The temperature inside the pipe 60 is kept lower than the boiling point of LNG (approximately −162° C.) and higher than the boiling point of nitrogen (approximately −177° C.). At this temperature, LNG is in the liquid phase, and nitrogen is in the gas phase. The inside of the housing 210 of the probe 20 is also referred to below simply as "inside the probe 20".

In this state, the valves b72, b74, b76, b78, along with the stop valve 240 and the windows 230 of the probe 20, are closed. The pressure of the nitrogen filling the housing 210 is higher than atmospheric pressure. Because of the nitrogen, the glass plate 222 and the windows 230 are pressed against the inner wall of the openings of the housing 210 facing the glass plate 222 and the windows 230. This reduces the risk of nitrogen leaking from the openings.

The maintenance PC 50 or another control apparatus may perform the control of the following steps.

Figure 5:
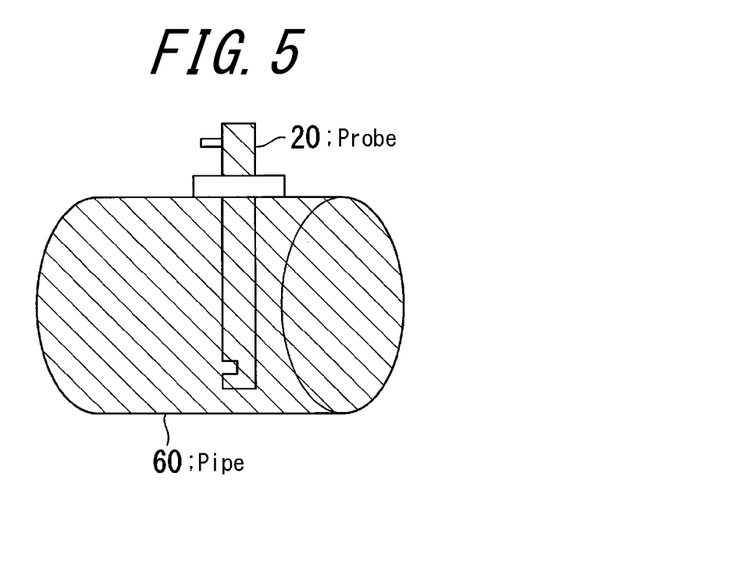
FIG. 5 illustrates the types of fluids in a probe and a pipe immediately after nitrogen is introduced into the pipe according to one or more embodiments.

(Step S102) A mechanism of the plant fills the pipe 60 in which the mechanism is disposed with nitrogen. In this state, both the inside of the probe 20 and the inside of the pipe 60 are filled with nitrogen (see FIG. 5). The processing proceeds to step S104.

(Step S104) The nitrogen filling the inside of the probe 20 is vacuumed. At this time, the stop valve 240, the valve b72, and the valve b74 of the probe 20 are opened. The vacuum pump 30 then suctions the nitrogen, via the conduit p80, for a predetermined time (such as 5 to 10 minutes). Subsequently, the processing proceeds to step S106.

(Step S106) The standard gas cylinder is connected to the conduit p80, and standard gas is introduced into the probe 20 from the connected standard gas cylinder. At this time, the valve b74 is closed, and operation of the vacuum pump 30 is suspended. With the valve b72 left open, the valve b78 and the stop valve 240 are opened for a predetermined time (such as 5 to 10 minutes). Subsequently, the valves b72, b78 and the stop valve 240 are closed, and the processing proceeds to step S108.

Figure 6:
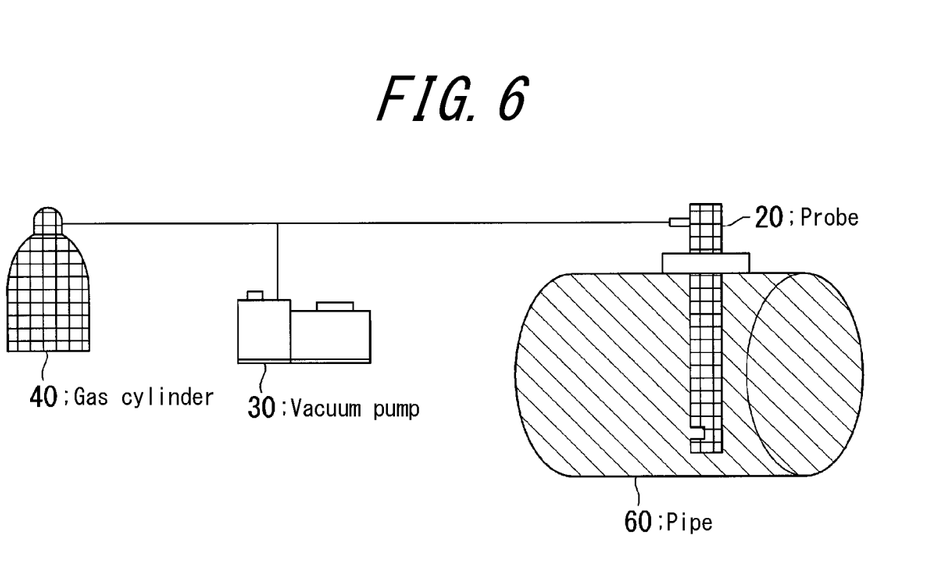
FIG. 6 illustrates the types of fluids in a probe and a pipe immediately after nitrogen in the probe is replaced with a standard gas according to one or more embodiments.

(Step S108) It is judged whether the nitrogen filling the inside of the probe 20 has been replaced by the standard gas. For example, it may be judged that the nitrogen has been replaced by the standard gas when the number of repetitions of steps S104 to S106 exceeds a predetermined threshold on the number of repetitions (such as 3 to 10 times). When it is judged that the nitrogen has been replaced (step S108: YES), the processing proceeds to step S110. In this state, the inside of the probe 20 is filled with the standard gas, and the inside of the pipe 60 is filled with nitrogen (FIG. 6). The cross-hatching in FIG. 6 represents the standard gas. When it is judged that the nitrogen has not been replaced (step S108: NO), the processing returns to step S104.

(Step S110) Based on the control by the maintenance PC 50, a testing unit of the FT-NIR 10 performs a hardware calibration test. The hardware includes the devices pertaining to the sequential path from light emission to detection, including the FT-NIR 10 itself, the optical fiber p82, and the probe 20. The test items performed in the calibration test include any one, or a predetermined combination, of a wavenumber stability test, a baseline stability test, a measurement light noise test, a measurement light linearity test, and the like. These test items are described below. When it is judged by the calibration test that a predetermined standard is satisfied, the processing proceeds to step S112. When it is judged by the calibration test that a predetermined standard is not satisfied, the processing of FIG. 3 may be interrupted, without proceeding to step S112 and onward.

(Step S112) The valves b72, b74, b78 and the stop valve 240 of the probe 20 are left closed, and the standard gas cylinder connected to the conduit p80 is changed to the nitrogen gas cylinder. Subsequently, the processing proceeds to step S114.

(Step S114) The standard gas filling the inside of the probe 20 is vacuumed. At this time, the valve b78 is left closed, and the valves b72, b74 and the stop valve 240 are opened. The vacuum pump 30 then suctions the standard gas, via the conduit p80, for a predetermined time (such as 5 to 10 minutes). Subsequently, the valves b72, b74 and the stop valve 240 of the probe 20 are closed, and the processing proceeds to step S116.

(Step S116) Nitrogen is introduced into the probe 20 from the nitrogen gas cylinder via the conduit p80. At this time, the valves b72, b78 and the stop valve 240 of the probe 20 are opened for a predetermined time (such as 5 to 10 minutes). Subsequently, the valves b72, b78 and the stop valve 240 are closed, and the processing proceeds to step S118.

Figure 7:
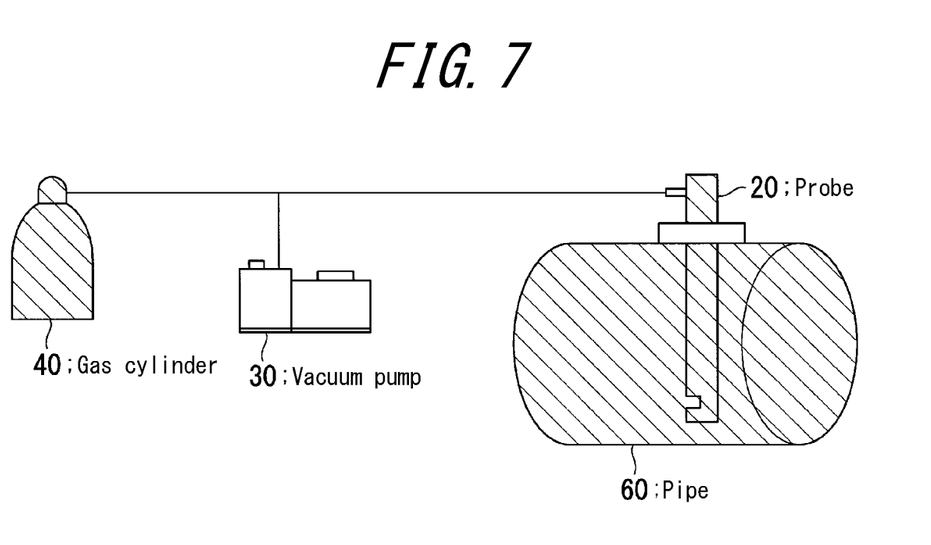
FIG. 7 illustrates the types of fluids in a probe and a pipe immediately after the standard gas in the probe is replaced with nitrogen according to one or more embodiments.

(Step S118) It is judged whether the standard gas filling the inside of the probe 20 has been replaced by nitrogen. For example, it may be judged that the standard gas has been replaced by nitrogen when the number of repetitions of steps S114 to S116 exceeds a predetermined threshold on the number of repetitions (such as 3 to 10 times). It may be judged whether the standard gas has been replaced by nitrogen by whether the absorption spectrum analyzed by the FT-NIR 10 has a peak in absorption at a characteristic wavelength for the standard gas. When it is judged that the standard gas has been replaced (step S118: YES), the processing proceeds to step S120. In this state, the inside of the probe 20 and the inside of the pipe 60 are filled with nitrogen (FIG. 7). When it is judged that the standard gas has not been replaced (step S118: NO), the processing returns to step S114.

Figure 8:
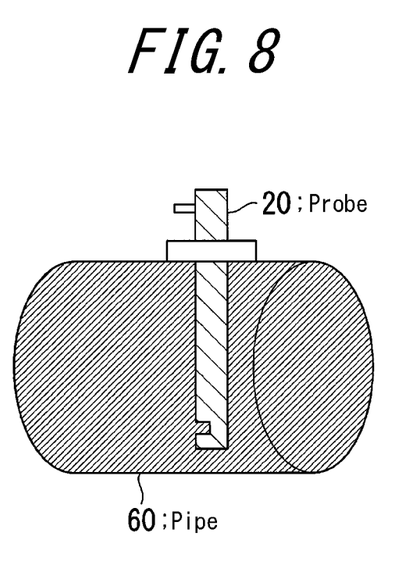
FIG. 8 illustrates the types of fluids in a probe and a pipe after LNG is introduced into the pipe according to one or more embodiments.

(Step S120) LNG is caused to flow again in the pipe 60. Consequently, the probe 20 is filled with nitrogen, whereas LNG flows in the pipe 60, as at the start of the processing in FIG. 3 (FIG. 8). The processing illustrated in FIG. 3 subsequently terminates.

Next, the test items of the calibration test performed by the maintenance PC 50 are described.

The wavenumber stability test is a test item for judging whether the wavenumber and width of a predetermined peak of the measured absorption spectrum are within predetermined standard ranges of the wavenumber [units: $cm^{-1}$] and width. One absorption spectrum may have a plurality of peaks. It suffices for at least one of the peaks to be the object of testing.

The baseline stability test is a test item for judging whether the average of the absorption [absolute value; Abs] in a predetermined range of wavenumbers of the measured absorption spectrum is within a predetermined standard range of averages. A known wavelength range at which a peak in the absorption spectrum is not detected is used as the range of wavenumbers of the object of testing.

The measurement light noise test is a test item for judging, from the absorption spectrum repeatedly measured a predetermined number of times (such as 2 to 6), whether the signal-to-noise (SN) ratio in a predetermined range of wavenumbers is greater than a predetermined reference SN ratio. For example, the average absorption of each wavenumber over the repeated measurement may be taken as the signal component, and the standard deviation of the absorption of each wavenumber may be taken as the noise component to calculate the ratio of the signal component to the noise component as the SN ratio. A known wavelength range at which a peak in the absorption spectrum is not detected is used as the range of wavenumbers of the object of testing of the wavelength absorption spectrum.

The measurement light linearity test is a test item for judging whether the ratio between the absorption of two predetermined peaks of the measured absorption spectrum is within an absorption ratio range serving as a predetermined standard. The wavelength of these two peaks is determined in advance. It is thereby determined whether the shape of the peak is within the range of a predetermined shape.

As described above, a testing method according to one or more embodiments is a testing method of the FT-NIR 10, which is an analysis apparatus that performs analysis using light incident through the probe 20. The probe 20 is attached to the pipe 60 in such a manner that a portion of the light path is disposed outside of the housing 210 and inside the pipe 60 through which the first fluid, which is the object of analysis, flows. The present testing method includes a first process (steps S104 to S108) of introducing a third fluid inside the housing 210 of the probe 20 in a state such that a second fluid that absorbs less of the light than the first fluid has been introduced into the pipe 60, the third fluid having known absorption characteristics. The present testing method includes a second process (step S110) of analyzing absorption characteristics of the third fluid using the incident light that has passed through the probe 20.

This configuration allows the sequence of hardware to be tested, without removal of the probe 20 from the pipe 60, by causing a portion of the light path to pass through the second fluid, which absorbs little light, and causing another portion of the light path to pass through the third fluid, which has known absorption characteristics. This test does not require the third fluid to be passed through the pipe 60, nor does it require the use of another measurement device. Accordingly, the testing efficiency of the sequence of hardware including the probe 20, the optical fiber p82, and the FT-NIR 10 can be improved.

A testing method according to one or more embodiments includes a third process (steps S112 to S118), after completion of the second process, of replacing the third fluid introduced inside the housing 210 with the second fluid.

With this configuration, the second fluid that absorbs little light can be introduced inside the housing 210, and the fluid that becomes the object of testing can be introduced inside the pipe 60, outside of the housing 210, to achieve a state allowing analysis of the fluid without the need to remove the probe 20 from the pipe 60. The operation efficiency until analysis begins again in the regular usage state after testing of the hardware can therefore be improved.

The housing 210 includes the measurement unit 212, which is a recess that is recessed (or depressed) inward from the surrounding area. A portion of the light path passes through the measurement unit 212.

This configuration divides the light path into a portion through which the second fluid passes and a portion through which the third fluid passes, even if the light path is a straight line. Consequently, fewer operations are necessary to arrange and adjust the positions of members that form the light path, such as the glass plate 222, the light guides 224-1, 224-2, the light guide holder 228, the windows 230, and the corner cube 232. The costs of manufacturing and adjusting the probe 20 are therefore reduced.

In a testing method according to one or more embodiments, the detection light is near-infrared light, and the second fluid is nitrogen. Nitrogen hardly absorbs near-infrared light and is optically stable. Therefore, nitrogen does not affect the testing results of the third fluid. Nitrogen is also a plentiful resource that allows economical testing.

In a testing method according to one or more embodiments, the first fluid flowing through the pipe 60 is in the liquid phase, and the second fluid and the third fluid introduced into the housing 210 are in the gas phase. This facilitates separation between the first fluid that is the target of analysis during regular measurement and the second fluid introduced into the pipe 60 during testing and also facilitates the exchange between the second fluid and the third fluid in the first process or the third process. The time and energy for testing are therefore reduced, and complicated processes are unnecessary. Since the second fluid and the third fluid that are exchanged in the probe 20 are in the gas phase, a sudden temperature change due to these fluids adhering to the members constituting the probe 20 is avoided. Accordingly, the risk of damage or destruction due to a temperature change is reduced.

Embodiments of the present invention have been described with reference to the drawings. Specific configurations, however, are not limited to the above-described embodiments, and a variety of design changes and the like can be made without departing from the spirit and scope of the present invention.

The case of the light emitted by the light source being near-infrared light has been described in the above embodiments, but the light may be visible light, ultraviolet light, or the like as long as the light includes a component having a wavelength in the range in which the first fluid that is the object of testing exhibits distinguishing absorption characteristics.

The second fluid is not limited to nitrogen, as long as the second fluid is chemically stable and has a significantly smaller absorption amount of light emitted by the light source than the first fluid. The second fluid may, for example, be helium (He). The boiling point of helium (approximately −269° C.) is also lower than the boiling point of LNG. A temperature range in which helium is in the gas phase while the first fluid is in the liquid phase therefore exists. Helium separates by vaporization in this temperature range.

In the probe 20 illustrated in FIG. 2, the light guide 224-2 and the corner cube 232 may be omitted, and a separate connector from the connector 220 may be provided at a position facing the intersecting surface, of the two intersecting surfaces forming the measurement unit 212, closer to the one end of the probe 20. One optical fiber p82 can be connected to this connector. On the other hand, it suffices for the other optical fiber p82 that emits light onto the light guide 224-1 to be connectable to the connector 220. In this configuration as well, a portion of the light path passes through the measurement unit 212, and another portion of the light path passes through the inside of the housing 210.

In the above-described embodiment, an example of the present invention being applied mainly to an LNG plant has been described, but the present invention may be applied to another plant that includes a pipe through which a fluid that is the target of analysis flows. The analysis apparatus is not limited to an FT-NIR and may be an analysis apparatus using a different measurement principle from a Fourier transform, such as distribution.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SIGNS LIST

1 Testing system
10 FT-NIR
20 Probe
30 Vacuum pump
40 Gas cylinder
50 Maintenance PC
210 Housing
212 Measurement unit
214 Flange
220 Connector
222 Glass plate
224 (224-1, 224-2) Light guide
226 (226-1, 226-2) Light path
228 Light guide holder
230 Window
232 Corner cube
240 Stop valve
242 Plug

The invention claimed is:

1. A method for testing an analysis apparatus that analyzes a first fluid flowing through a pipe using light that has passed through a probe attached to and disposed inside the pipe such that a portion of a light path passes outside a housing of the probe, the method comprising:
after a second fluid that absorbs less of the light than the first fluid has been introduced into the pipe, introducing a third fluid having predetermined absorption characteristics into the housing; and
analyzing the absorption characteristics of the third fluid using the light that has passed through the probe.

2. The method of claim 1, further comprising:
after the analyzing of the absorption characteristics of the third fluid, replacing the third fluid inside the housing with the second fluid.

3. The method of claim 1, wherein
the housing comprises a recess that is depressed inward into the housing; and
the portion of the light path passes through the recess.

4. The method of claim 1, wherein
the light is near-infrared light; and
the second fluid is nitrogen.

5. The method of claim 1, wherein
the first fluid flowing through the pipe is in a liquid phase; and
the second fluid and the third fluid introduced into the housing are in a gas phase.

6. A system for testing an analysis apparatus that analyzes a first fluid flowing through a pipe using light that has passed through a probe attached to and disposed inside the pipe such that a portion of a light path passes outside a housing of the probe, the system comprising:
a first container that contains a second fluid that absorbs less of the light than the first fluid;
a second container that contains a third fluid that has predetermined absorption characteristics;
a conduit that introduces the second fluid or the third fluid into the housing and introduces the third fluid into the housing after the second fluid has been introduced into the pipe; and
the analysis apparatus that analyzes the absorption characteristics of the third fluid using the light that has passed through the probe.

7. The system of claim 6, further comprising:
a pump that sucks the second fluid or the third fluid introduced into the housing.

8. The method of claim 1, wherein
the analyzing comprises:
detecting the light;
deriving an absorption spectrum by calculating absorption as a ratio of an intensity of emitted light to an intensity of the detected light; and
determining whether the absorption spectrum satisfies a predetermined standard.

9. The system of claim 7, wherein after the analysis apparatus analyzes the absorption characteristics of the third fluid, the pump sucks the third fluid introduced into the housing and the conduit introduces the second fluid via the first container into the housing, resulting in replacing the third fluid inside the housing with the second fluid.

10. The system of claim 6, further comprising a maintenance personal computer (PC), wherein the analysis apparatus analyzes the absorption characteristics of the third fluid by:
- detecting the light; and
- deriving an absorption spectrum by calculating absorption as a ratio of an intensity of emitted light to an intensity of the detected light, and
- the maintenance PC determines whether the absorption spectrum satisfies a predetermined standard.

* * * * *